United States Patent [19]

Carlock

[11] 4,183,825
[45] Jan. 15, 1980

[54] METHOD FOR THE ACTIVATION OF POLYMER-BOUND BIS(TRIPHENYLPHOSPHINE)RHODIUM CARBONYL HALIDE HYDROFORMYLATION CATALYSTS

[75] Inventor: John T. Carlock, Ponco City, Okla.

[73] Assignee: Conoco, Inc., Ponca City, Okla.

[21] Appl. No.: 924,597

[22] Filed: Jul. 14, 1978

[51] Int. Cl.$^2$ .................... B01J 31/24; B01J 23/46; B01J 27/10; C07C 45/02

[52] U.S. Cl. .................... 252/429 R; 252/431 P; 260/604 HF

[58] Field of Search ........... 252/431 P, 431 N, 431 C, 252/431 R, 428, 429 R; 526/27

[56] References Cited

U.S. PATENT DOCUMENTS 3,944,603 3/1976 Morris .............................. 252/431 R
4,052,461 10/1977 Tinker et al. ........................ 252/432

OTHER PUBLICATIONS

Annals of the New York Academy of Science; 239,76 (1974), Pittman et al.

*Primary Examiner*—P. E. Konopka
*Attorney, Agent, or Firm*—Cortlan R. Schupbach, Jr.

[57] ABSTRACT

Polymer-bound bis(triphenylphosphine)rhodium or iridium carbonyl halide can be activated for use as a hydroformylation catalyst by treatment with a non-complexing base, particularly NaBPh$_4$ (where Ph=phenyl or C$_6$H$_5$ moiety) in a suitable polar solvent for an appropriate period of time. Such treated compounds are immediately active as hydroformylation catalysts under reaction conditions of about 50 to about 3500 psig of a hydrogen-carbon monoxide gas mixture and about 60° to about 150° C. temperature.

6 Claims, No Drawings

METHOD FOR THE ACTIVATION OF POLYMER-BOUND BIS(TRIPHENYLPHOSPHINE)RHODIUM CARBONYL HALIDE HYDROFORMYLATION CATALYSTS

This invention relates to a method for increasing the hydroformylation activity of hydroformylation catalysts. More particularly, this invention relates to a method of immediately activating polymer-bound bis(triphenylphosphine) rhodium or iridium carbonyl halides for use as a hydroformylation catalyst by treatment with a non-complexing base in a suitable polar solvent for an appropriate length of time.

The hydroformylation of terminal or alpha olefins by certain rhodium catalysts is known in the art. Representative examples describing rhodium catalysts used in hydroformylation reactions and reaction conditions necessary are found in U.S. Pat. Nos. 3,917,661; 3,907,847; 3,821,311; 3,499,932; 3,527,809; 3,825,601; 3,948,999; and 3,984,478. Literature references of polymer-bound catalysts include *Tetrahedron Letters*, 1971 (50) 4787-90, Grubbs et al, Journal of *Macrmol. Sci. Chem.*, 1972, 13 (12), 828-32. While these references are not exhaustive of the art they appear to be representative of hydroformylation in the current state of the art.

However, bis(triphenylphosphine)rhodium carbonyl halides represent the most inexpensive of rhodium or iridium carbonyl compounds due to their easy synthesis from rhodium or iridium trihalides. Once reduced, such compounds are precursors to active hydroformylation intermediates. However, under normal hydroformylation reaction conditions, such a reduction is kinetically not favored, and until the halide is removed from the rhodium or iridium coordination sphere, the complex is inactive in the hydroformylation sequence. This results in a characteristically observed induction period when polymerbound bis(triphenylphosphine)rhodium carbonyl halides or their iridium counterparts are employed in hydroformylation reactions. Such induction periods result in very large reaction space numbers, making processes which employ such catalysts initially uneconomical from an industrial viewpoint.

Hydroformylation is a reaction which converts olefins to aldehydes. Usually the hydroformylation procedure is followed by the hydrogenation of aldehydes to produce alcohol. However, the hydrogenation procedure is relatively simple and can be carried by any one of several well known means.

Bis(triphenylphosphine)metal carbonyl halides described above can be bound to polymers for better results. Synthesis of a polymer-bound bis(triphenylphosphine)rhodium carbonyl halide has been shown in the *Ann N.Y. Acad. Sci.*, 239,76 (1974) by Pittman et al. However, this reference does not suggest a method for activating such catalysts to immediate activity. It would be of great benefit to immediately activate such a catalyst in order to achieve immediate hydroformylation results.

It is therefore an object of the present invention to provide a method for the activation of polymer-bound bis(triphenylphosphine)metal carbonyl halide catalysts. Other objects will become apparent to those skilled in this art as the description proceeds.

It has now been discovered in accordance with the instant invention that polymer-bound bis(triphenylphosphine)-rhodium or iridium carbonyl halide catalyst can be activated by treatment with any non-complexing base in an appropriately polar solvent. The catalysts so created are observed not only to be instantly active in hydroformylation reactions but also to have increased activity over non-treated polymer-bound bis(triphenylphosphine)rhodium carbonyl chloride catalysts which had been allowed to come to their full activity after proceeding through a reaction induction period.

The instant method thus provides a method for increasing the hydroformylation activity of bis(triphenylphosphine) metal carbonyl halides bound to diphenylphosphinated polystyrene/divinylbenzene copolymers comprising treating the catalyst with a non-complexing base in a polar solvent capable of dissolving said base and of swelling said polymer, and refluxing the solution so obtained to form a catalyst of the general structure

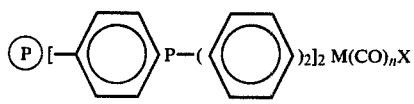

wherein M is rhodium or iridium, n is sufficient to satisfy valence, usually 1, and X is bromine, chlorine, or iodine. The polar solvent should be oxygen-free and non-chlorinated for best effects. The total number of groups coordinately bonded to M is no greater than 6 or less than 4.

The activation procedures will also be effective when the non-complexing base is added directly to the reaction vessel with the untreated catalyst in a polymer swelling solvent and heating and pressurizing the reactor with a hydrogen/carbon monoxide mixture. This method is especially suitable for tertiary amines.

In general, any solvent which is oxygen-free and which will dissolve the non-complexing base without harming the catalyst (preferably non-chlorinated solvents) will be effective. As the solvent of choice, an amount of swelling solvent sufficient to swell the polymer is added but not sufficient to precipitate non-complexing base. For example, solvents such as methanol, propanol, ethanol, acetone, dimethylformamide (DMF), and dimethylsulfoxide (DMSO) will be effective. In addition, other solvents such as tetrahydrofuran (THF) will be effective in an admixture with sufficient swelling solvent to allow access to the entire polymer.

Representative examples of suitable non-complexing bases are hydrous and anhydrous, potassium acetate, sodium acetate, potassium formate, sodium formate, potassium benzoate, sodium benzoate, sodium tetraphenylborate, potassium tetraphenylborate, sodium and potassium salts of all non-complexing carboxylic acids, alkaline earth salts of all non-complexing carboxylic acids, sodium or potassium phosphate, sodium sulfate, potassium sulfate, alkali salts of phosphorus and sulfur-containing acids, alkaline earth salts of sulfur and phosphorus-containing acids, alkali salts of boron-containing acids, alkaline earth salts of boron containing acids, triethylamine, trimethylamine, tripropylamine, and other non-complexing tertiary amines.

In the case of sodium tetraphenylborate the effect generated by the process of the instant invention is possibly due to carbonyl ligand protonation of one of the hydroformylation reaction intermediates by species generated in-situ from the tetraphenylborate anion. This subsequently results in a weaker metal hydrogen bond thus lowering the catalyst's energy of activation and allowing the reaction to proceed under milder conditions. However, it is emphasized that the hypothesis is that devised to explain the process of the instant invention and I do not wish to be bound thereby. However, when the process of the instant invention is carried out, the reaction induction period is eliminated and the treated catalyst shows increased hydroformylation activity. This is greatly important since the invention makes use of the relatively inexpensive polymer-bound bis(triphenylphosphine)metal carbonyl halides which are easily made and economically feasible for use in industrial scale hydroformylation reactions.

The invention is more concretely described with reference to the examples below wherein all parts and percentages are by weight unless otherwise specified. The examples are provided to illustrate the instant invention and not to limit it. Example 1 shows a preparation of a treated catalyst. Example 2 shows the use of the treated catalyst in a typical hydroformylation reaction. Example 3 is a comparative example showing an untreated catalyst in an identical reaction as carried out in Example 2. Example 4 shows the recovered catalyst from Example 2. Examples 5 and 6 show further recoveries of the same catalyst. All reaction sequences and catalyst transfers were carried out under an oxygen-free inert atmosphere. Solvents employed were deoxygenated before use.

EXAMPLE 1

A polymer-bound bis(triphenylphosphine)rhodium carbonyl halide catalyst was synthesized according to Pittman et al, *Ann. N.Y. Acad. Sci.*, 239, 76 (1974). The catalyst obtained (10 grams) was added to a solution of 4 grams of sodium tetraphenylborate in 50 ml of tetrahydrofuran. The mixture was stirred for 240 hours then refluxed for 6 hours. Then the mixture was filtered, extracted with tetrahydrofuran for 18 hours and dried under vacuum at 25° C. for 10 hours. Analysis of the product revealed that the catalyst contained 1.2% chlorine, 5.2% phosphorus, 5.4% rhodium and 0.13% boron. Spectroscopic analysis performed on the product revealed the chloride to be present as sodium chloride.

EXAMPLE 2

A general hydroformylation reaction using the catalyst described in Example 1 was carried out. Two grams of the treated catalysts and 10 ml of benzene was charged into an autoclave equipped with a magnetic stirring bar. The autoclave was sealed, placed in a dry ice-acetone slush cooling bath and charged with 35 grams of 1-butene gas. The autoclave was then placed upon a magnetic stirring bar drive motor equipped with a heating block. The reactor was then quickly heated, with stirring to 100° C. at which temperature the reaction pressure gauge read 150 psig from the combined expansion of the 1-butene and solvent. 100 psig of a 1:1 hydrogen-carbon monoxide gas mixture was then added in addition to the existing reactor internal pressure to give a combined reading of 250 psig. This pressure was maintained throughout the course of the reaction. After 3.33 hours of reaction time the autoclave was returned to the argon-filled dry box, cooled to −10° C., opened and the catalyst removed from the reaction mixture by filtration. Chemical and physical analysis using GLC and means of the reaction mixture indicated a 92% conversion of 1-butene to $C_5$ aldehydes. The product contained a normal to isomerized aldehyde ratio of 10.28.

EXAMPLE 3

A sample of untreated catalyst was used in a reaction identical to that of Example 2. A 2-gram sample of untreated polymer-bound bis(triphenylphosphine)rhodium carbonyl chloride having an equal rhodium content (5.4%) prepared according to the reference in Example 1 was used in a reaction identical with that described in Example 2. After 3.33 hours of reaction time analysis of the reaction product indicated only a 10% conversion of 1-butene to $C_5$ aldehydes, the product having a normal to isomerized product ratio of 2.5.

EXAMPLE 4

The catalyst was recovered from Example 2 by filtration and employed in an experiment identical with Example 2 except that the reation temperature was maintained at 90° C. and only 50 psig of a 1:1 hydrogen/carbon monoxide gas mixture was used in addition to the olefin and solvent pressures at maximum temperature. After 4.83 hours of reaction time analysis of the reaction mixture indicated a 40% conversion of 1-butene to $C_5$ aldehydes having a normal to isomerized product ratio of 14.35. It is apparent that while greater reaction pressures and temperatures are necessary for higher olefin conversions, less drastic conditions result in a higher normal to isomerized aldehyde product ratio.

EXAMPLE 5

The catalyst was recovered from Example 4 by filtration and recharged into an autoclave. A reaction was then carried out identically as described in Example 2 except that 125 psig of a 1:1 hydrogen/carbon monoxide gas mixture was used. The reaction temperature was maintained at 105° C. After 6.2 hours of reaction time, analysis of the reaction mixture indicated a 90% conversion of 1-butene to $C_5$ aldehydes. The reaction product had a normal to isomerized product ratio of 5.88. Thus it is apparent that increased pressures and reaction temperatures result in a lower normal to isomerized product ratio than observed with the milder conditions described in Examples 2 and 4.

EXAMPLE 6

The catalyst was recovered from Example 5 by filtration and recharged into an autoclave. Identical reaction conditions were carried out as used in Example 2 except that the reaction temperature was maintained at 90° C. and the 1:1 hydrogen/carbon monoxide gas pressure was maintained at 85 psig (above reactors internal pressure at the maximum temperature). After 21.88 hours of reaction time analysis of the reaction product indicated a 71% conversion of 1-butene to $C_5$ aldehydes. The product had a normal to isomerized product ratio of 4.89. The Example illustrates that when energetically insufficient reaction conditions are presented to the treated catalyst, and the reaction is allowed to proceed over an extended period of time, isomerization of the alpha-olefin feedstock becomes a competing reaction with hydroformylation resulting in reduced yields and lowered normal to isomerized aldehyde product ratios.

EXAMPLE 7

Two grams of untreated catalyst, identical to that used in Example 3, is charged into an autoclave with 20 ml of benzene swelling solvent and an amount of trioctylamine identical in molar quantity to the amount of chloride present in the untreated polymer catalyst. Thirty-five grams of 1-butene are added and the reaction is then carried out identically as in Example 2.

This reaction is seen to progress much more rapidly than the reaction described in Example 3 with the untreated catalyst, indicating catalyst activation through the use of this procedure.

EXAMPLE 8

In order to quantify metal elution from the polymer the reaction products from each example were analyzed for dium content using X-ray fluorescence techniques. Resulting data is presented together with a summary of each example in Table 1.

Table 1

| Example | Reaction Sequence | Catalyst | % Conversion/ Reaction Time (Hr) | n/i | °C./ Pressure (psig) | Rhodium Elution (ppm) |
| --- | --- | --- | --- | --- | --- | --- |
| 2 | 1 | Treated | 92/3.333 | 10.28 | 100/100 | 3.4 |
| 3 | — | Untreated | 10/3.333 | 2.85 | 100/100 | — |
| 4 | 2 | Treated | 40/4.833 | 14.35 | 90/50 | 28.0 |
| 5 | 3 | Treated | 90/6.216 | 5.88 | 105/125 | 1.8 |
| 6 | 4 | Treated | 71/21.883 | 4.89 | 90/85 | 1.9 |

The treated catalyst of the instant invention are immediately active as hydroformylation catalysts under reaction conditions of from about 50 to about 3500 psig under a hydrogen/carbon monoxide atmosphere. Reaction temperatures range from about 60° to about 150° C. Higher reaction temperatures are possible as the pressure exceeds about 2500 psig. Pressures can range up to about 3500 psig limited usually only by reactor material considerations.

The hydroformylation is carried out in the presence of mixtures of hydrogen and carbon monoxide. It is necessary for 1 mole of hydrogen/carbon monoxide to be present for every mole of olefin converted. However, the ratio of hydrogen to carbon monoxide will range from about 1:100 to about 100:1, although from about 80:20 to about 20:80 respectively is preferred, and from about 60:40 to about 50:50 is more preferred and 50:50 respectively is most preferred.

Thus the invention provides a simple and efficient method for immediately activating easily prepared hydroformylation catalysts to maximum activity. The catalysts are efficient under normal hydroformylation conditions.

While certain embodiments and details have been shown for the purpose of illustrating this invention, it will be apparent to those skilled in this art that various changes and modifications may be made herein without departing from the spirit or scope of the invention.

I claim:

1. A method for increasng the hydroformylation activity of a catalyst of the general structure

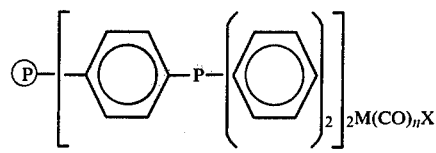

comprising treating the catalyst with a non-complexing base in a polar solvent capable of dissolving said base and swelling said polymer and refluxing the solution so obtained, and wherein M is rhodium or iridium, n is sufficient to satisfy metal valence, and X is bromine, chlorine, or iodine and (P) is a polyvinyl pyridine/divinylbenzene copolymer.

2. A method as described in claim 1 wherein M is rhodium and n is 1.

3. A method as described in claim 2 wherein the solvent is selected from the group consisting of methanol, propanol, butanol, acetone, dimethylformamide, dimethylsulfoxide, or mixtures of these.

4. A method as described in claim 3 wherein the solvent used is capable of dissolving a non-complexing base and swelling the catalyst.

5. A method as described in claim 4 wherein the non-complexing base is selected from the group consisting of hydrous or anhydrous, potassium acetate, sodium acetate, potassium formate, sodium formate, potassium benzoate, sodium benzoate, sodium tetraphenylborate, potassium tetraphenylborate, sodium phosphate, potassium phosphate, sodium sulfate, potassium sulfate, triethylamine, trimethylamine, tripropylamine, sulfonic acid salts, boric acid salts, all tributylamines, triphenylamines, all trihexyl, trioctyl, tri $C_9$-$C_{40}$ amines, sodium and potassium salts of non-complexing carboxylic acid, and alkaline earth salts of non-complexing carboxylic acid.

6. A method as described in claim 1 wherein the total number of groups coordinately bonded to M is no greater than 6 or less than 4.

* * * * *